United States Patent [19]

Machin et al.

[11] Patent Number: 4,774,253

[45] Date of Patent: Sep. 27, 1988

[54] OXAZOLE AND ISOXAZOLE DERIVATIVES HAVING ANTI-ARTHRITIC ACTIVITY

[75] Inventors: Peter J. Machin, London; John M. Osbond, Hatfield; Christopher R. Self, Hitchin; Carey E. Smithen, Welwyn Garden City; Brian P. Tong, Harpenden, all of England

[73] Assignee: Hoffmann-La Roche Inc., Nutley, N.J.

[21] Appl. No.: 917,566

[22] Filed: Oct. 10, 1986

[30] Foreign Application Priority Data

Oct. 17, 1985 [GB] United Kingdom ............... 8525578
Jul. 17, 1986 [GB] United Kingdom ............... 8617503

[51] Int. Cl.$^4$ .................. A61K 31/42; C07D 261/06; C07D 263/30
[52] U.S. Cl. .................................. 514/374; 514/378; 546/209; 548/215; 548/236; 548/240; 548/248; 548/249
[58] Field of Search ............... 548/215, 235, 236, 240, 548/247, 248, 249; 514/374, 378; 546/209

[56] References Cited

U.S. PATENT DOCUMENTS

| | | | |
|---|---|---|---|
| 3,470,195 | 9/1969 | O'Mant | 548/235 |
| 3,642,812 | 2/1972 | Southern | 548/247 |
| 3,652,575 | 3/1972 | Hutton | 548/235 |
| 4,460,596 | 7/1984 | Matsumoto | 514/374 |

OTHER PUBLICATIONS

GCr 140838, D. P. Bloxham et al., Aug. 17, 1987.
GCr 140943, C. R. Self et al., Jan. 25, 1988.
Wyeth, Derwent No. 72056X, 7/9/76.
Hisamitsu, Derwent No. 85-300551, 21/10/85.
Ici, Derwent No. 30027F, 27/12/67.
S. J. Foster et al., Biochem. Pharmacol., 1983, 32(3), pp. 461–467.
Roche/Roche/Roche, Scrip No. 1145, Oct. 13, 1986, p. 27.

*Primary Examiner*—Donald G. Daus
*Assistant Examiner*—Mark W. Noel
*Attorney, Agent, or Firm*—Jon S. Saxe; Bernard S. Leon; Matthew Boxer

[57] ABSTRACT

Oxazole and isoxazole derivatives of the formula

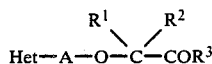

wherein A is $C_{1-6}$-alkylene, Het is a 2-R-oxazol-5-yl, 5-R-oxazol-2-yl, 4-R-oxazol-2-yl, 2-R-oxazol-4-yl, 3-R-isoxazol-5-yl or 5-R-isoxazol-3-yl group which is optionally substituted on the heterocyclic ring by a $C_{1-6}$-alkyl group, R is phenyl or thienyl monosubstituted or disubstituted by halogen, trifluoromethyl or $C_{1-6}$-alkylthio, $R^1$ and $R^2$ each is a $C_{1-6}$-alkyl group and $R^3$ is a hydroxy or $C_{1-6}$-alkoxy group or a group of the formula $-NR^4R^5$ in which $R^4$ and $R^5$ each is a hydrogen atom or a $C_{1-6}$-alkyl group or $R^4$ and $R^5$ together with the nitrogen atom to which they are attached is a 5-membered or 6-membered saturated heteromonocyclic ring which may contain an oxygen or sulphur atom or an additional nitrogen atom, and pharmaceutically acceptable salts of the compounds of formula I in which $R^3$ is a hydroxy group with bases, have anti-arthritic activity.

18 Claims, No Drawings

OXAZOLE AND ISOXAZOLE DERIVATIVES HAVING ANTI-ARTHRITIC ACTIVITY

BRIEF SUMMARY OF THE INVENTION

Oxazole and isoxazole derivatives of the formula

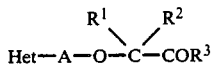   I wherein A is $C_{1-6}$-alkylene, Het is a 2-R-oxazol-5-yl, 5-R-oxazol-2-yl, 4-R-oxazol-2-yl, 2-R-oxazol-4-yl, 3-R-isoxazol-5-yl or 5-R-isoxazol-3-yl group which is optionally substituted on the heterocyclic ring by a $C_{1-6}$-alkyl group, R is phenyl or thienyl monosubstituted or disubstituted by halogen, trifluoromethyl or $C_{1-6}$-alkylthio, $R^1$ and $R^2$ each is a $C_{1-6}$-alkyl group and $R^3$ is a hydroxy or $C_{1-6}$-alkoxy group or a group of the formula $-NR^4R^5$ in which $R^4$ and $R^5$ each is a hydrogen atom or a $C_{1-6}$-alkyl group or $R^4$ and $R^5$ together with the nitrogen atom to which they are attached is a 5-membered or 6-membered saturated heteromonocyclic ring which may contain an oxygen or sulphur atom or an additional nitrogen atom, and pharmaceutically acceptable salts of the compounds of formula I in which $R^3$ is a hydroxy group with bases, are described. The compounds of formula I are useful as agents in the control or prevention of arthritis.

DETAILED DESCRIPTION OF THE INVENTION

The invention relates to heterocyclic compounds.

More particularly, the invention is concerned with oxazole and isoxazole derivatives of the formula

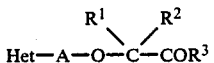   I wherein A is $C_{1-6}$-alkylene, Het is a 2-R-oxazol-5-yl, 5-R-oxazol-2-yl, 4-R-oxazol-2-yl, 2-R-oxazol-4-yl, 3-R-isoxazol-5-yl or 5-R-isoxazol-3-yl group which is optionally substituted on the heterocyclic ring by a $C_{1-6}$-alkyl group, R is phenyl or thienyl monosubstituted or disubstituted by halogen, trifluoromethyl or $C_{1-6}$-alkylthio, $R^1$ and $R^2$ each signify a $C_{1-6}$-alkyl group and $R^3$ is a hydroxy or $C_{1-6}$-alkoxy group or a group of the formula $-NR^4R^5$ in which $R^4$ and $R^5$ each is a hydrogen atom or a $C_{1-6}$-alkyl group or $R^4$ and $R^5$ together with the nitrogen atom to which they are attached is a 5-membered or 6-membered saturated heteromonocyclic ring which may contain an oxygen or sulphur atom or an additional nitrogen atom, and pharmaceutically acceptable salts of the compounds of formula I in which $R^3$ is a hydroxy group with bases.

These compounds possess valuable pharmacological properties and can be used in the control or prevention of illnesses. In particular, they have anti-arthritic activity and can be used as agents in the control or prevention of arthritis.

Objects of the invention are the aforementioned compounds of formula I and pharmaceutically acceptable salts thereof per se and for use as therapeutically active substances, a process for the manufacture of these compounds and salts, medicaments containing a compound of formula I or a pharmaceutically acceptable salt thereof, the use of the compounds of formula I and their pharmaceutically acceptable salts in the control or prevention of illnesses, as well as their use for the manufacture of medicaments having anti-arthritic activity.

As used in this Specification, the term "$C_{1-6}$-alkyl", alone or in combination, means straight-chain or branched-chain alkyl groups containing from 1 to 6, preferably from 1 to 4, carbon atoms such as methyl, ethyl, propyl, isopropyl, butyl, sec.butyl, tert.butyl, pentyl and hexyl. The term "$C_{1-6}$-alkoxy" means an alkyl ether group containing from 1 to 6, preferably from 1 to 4, carbon atoms such as methoxy, ethoxy, propoxy, isopropoxy, butoxy, tert.butoxy etc. The term "$C_{1-6}$-alkylene" means a straight-chain or branched-chain alkylene group containing from 1 to 6, preferably from 1 to 4, carbon atoms such as methylene ($-CH_2-$), 1,1-ethylene [$-CH(CH_3)-$], 1,2-ethylene ($-CH_2CH_2-$), 1,3-propylene [$-(CH_2)_3-$], 1,4-butylene [$-(CH_2)_4-$] and the like. The $C_{1-6}$-alkylthio group can be, for example, methylthio or ethylthio. Examples of groups of the formula $-NR^4R^5$ in which $R^4$ and $R^5$ each is a hydrogen atom or a $C_{1-6}$-alkyl group are amino, methylamino, ethylamino, dimethylamino, diethylamino etc. When $-NR^4R^5$ is a saturated heteromonocyclic ring as defined earlier, this can be, for example, a pyrrolidino, piperazino, morpholino, thiamorpholino or like ring. The term "halogen" means fluorine, chlorine, bromine or iodine.

The structures and ring-numbering for

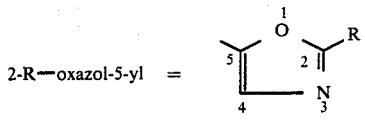

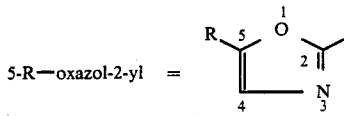

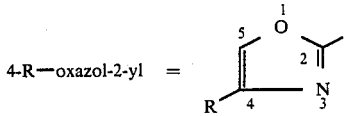

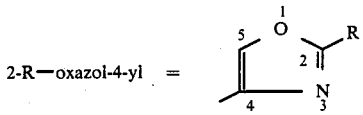

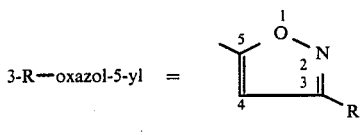

and

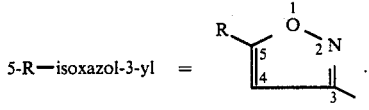

The $C_{1-6}$-alkyl groups denoted by $R^1$ and $R^2$ in formula I can be the same or different. Further, when R is disubstituted-phenyl or disubstituted-thienyl, the substituents can be the same or different.

It will be appreciated that when $R^1$ and $R^2$ are different $C_{1-6}$-alkyl groups or when A is branched-chain $C_{1-6}$-alkylene the compounds of formula I contain an asymmetric carbon atom and can accordingly exist in racemic or optically active form. Further, when two asymmetric carbon atoms are present the compounds can exist as diastereomers. The invention is intended to embrace not only the optically active enantiomers of such compounds, but also the racemates and diastereomers.

In formula I above A preferably is methylene, 1,1-ethylene or 1,2-ethylene, Het preferably is a 2-R-oxazol-5-yl group which is optionally substituted by a $C_{1-6}$-alkyl group, especially methyl. R preferably is monohalophenyl, especially monochlorophenyl and particularly 4-chlorophenyl. $R^1$ and $R^2$ each preferably is methyl. $R^3$ preferably is hydroxy.

Especially preferred compounds of by the invention are:

2-[[2-(4-Chlorophenyl)-4-methyl-5-oxazolyl]methoxy]-2-methylpropionic acid and sodium 2-[[2-(4-chlorophenyl)-4-methyl-5-oxazolyl]methoxy]-2-methylpropionate.

The first of the two just above named compounds is a carboxylic acid, that is $R^3$ is hydroxy, while the second compound is the sodium salt of the first compound.

Other compounds of the present invention are:

2-[[2-(4-Fluorophenyl)-4-methyl-5-oxazolyl]methoxy]-2-methylpropionic acid,

2-[[2-(4-trifluoromethylphenyl)-4-methyl-5-oxazolyl]methoxy]-2-methylpropionic acid, 2-[[2-(4-chlorophenyl)-5-oxazolyl]methoxy]-2-methylpropionic acid, 2-[[5-(4-chlorophenyl)-2-oxazolyl]methoxy]-2-methylpropionic acid, 2-[[4-(4-chlorophenyl)-2-oxazolyl]methoxy]-2-methylpropionic acid, 2-[[2-(4-trifluoromethylphenyl)-5-methyl-4-oxazolyl]methoxy]-2-methylpropionic acid, 2-[[2-(4-chlorophenyl)-5-methyl-4-oxazolyl]methoxy]-2-methylpropionic acid, 2-[[2-(4-fluorophenyl)-5-methyl-4-oxazolyl]methoxy]-2-methylpropionic acid, 2-[[2-(4-chlorophenyl)-4-oxazolyl]methoxy]-2-methylpropionic acid, 2-[[2-(3,4-dichlorophenyl)-4-methyl-5-oxazolyl]methoxy]-2-methylpropionic acid, 2-[[2-(3-chlorophenyl)-4-methyl-5-oxazolyl]methoxy-2-methylpropionic acid, 2-methyl-2-[[4-methyl-2-[4-(methylthio)phenyl]-5-oxazolyl]methoxy]propionic acid, 2-[[2-(4-chlorophenyl)-4-methyl-5-oxazolyl]methoxy]-2-methylpropionamide, ethyl 2-[[2-(4-chlorophenyl)-4-methyl-5-oxazolyl]methoxy]-2-methylpropionate, 2-[[2-(4-chlorophenyl)-4-ethyl-5-oxazolyl]methoxy]-2-methylpropionic acid, 2-[[2-(4-chlorophenyl)-4-methyl-5-oxazolyl]methoxy]-2-ethylbutyric acid, 2-[2-[2-(4-chlorophenyl)-4-methyl-5-oxazolyl]ethoxy]-2-methylpropionic acid, 2-[[2-(4-chlorophenyl)-4-methyl-5-oxazolyl]methoxy]-2-methylbutyric acid and methyl 2-[[2-(4-chlorophenyl)-4-methyl-5-oxazolyl]methoxy]-2-methylpropionate.

Examples of other compounds of the present invention are:

2-[[3-(4-Chlorophenyl)-5-isoxazolyl]methoxy]-2-methylpropionic acid,

2-[[5-(4-chlorophenyl)-3-isoxazolyl]methoxy]-2-methylpropionic acid, methyl 2-[[3-(4-chlorophenyl)-5-isoxazolyl]methoxy]-2-methylpropionate, 2-[2-[3-(4-chlorophenyl)-5-isoxazolyl]ethoxy]-2-methylpropionic acid, methyl 2-[[3-(3,4-dichlorophenyl)-5-isoxazolyl]methoxy]-2-methylpropionate, 2-[[3-(3,4-dichlorophenyl)-5-isoxazolyl]methoxy]-2-methylpropionic acid, 2-[1-[3-(4-chlorophenyl)-5-isoxazolyl]ethoxy]-2-methylpropionic acid, 2-[[3-(5-chlorothien-2-yl)-5-isoxazolyl]methoxy]-2-methylpropionic acid, 2-[[3-(4-chlorophenyl)-5-isoxazolyl]methoxy]-2-methylpropionamide, 2-[[3-(4-chlorophenyl)-5-isoxazolyl]methoxy]-N,2-dimethylpropionamide and 3-(4-chlorophenyl)-5-[[1-methyl-1-(piperidinocarbonyl)ethoxy]methyl]isoxazole.

According to the process of the present invention, the compounds of formula I and pharmaceutically acceptable salts of the compounds of formula I in which $R^3$ is a hydroxy group with bases are prepared by (a) for making a compound of formula I in which $R^3$ is a hydroxy group, reacting an alcohol of the formula

Het—A—OH      II wherein A and Het are as described above, with a ketone of the formula

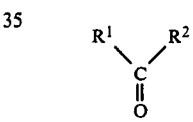

III wherein $R^1$ and $R^2$ are as described above, in the presence of a trihalogenated or tetrahalogenated alkane and a strong base, or (b) for making a compound of formula I in which $R^3$ is a $C_{1-6}$-alkoxy group or a group of the formula —$NR^4R^5$ in which $R^4$ and $R^5$ are as described above, reacting a compound of the formula

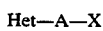

Het—A—X      IV with a compound of the formula

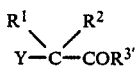

V wherein A, Het, $R^1$ and $R^2$ are as described above, one of X and Y is a hydroxy group and the other is a leaving atom or group and $R^{3'}$ is a $C_{1-6}$-alkoxy group or a group of the formula —$NR^4R^5$ in which $R^4$ and $R^5$ are as described above, in the presence of a strong base, or (c) for making a compound of formula I in which Het is a 3-R-isoxazol-5-yl group and $R^3$ is a $C_{1-6}$-alkoxy group, reacting a compound of the formula

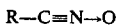

R—C≡N→O      VI wherein R is as described above, with a compound of the formula

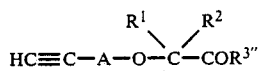

wherein A, $R^1$ and $R^2$ are as described above and $R^{3''}$ is a $C_{1-6}$-alkoxy group, or (d) for making a compound of formula I in which $R^3$ is a hydroxy group, hydrolyzing a compound of formula I in which $R^3$ is a $C_{1-6}$-alkoxy group, or (e) for making a compound of formula I in which $R^3$ is a $C_{1-6}$-alkoxy group, appropriately esterifying a compound of formula I in which $R^3$ is a hydroxy group, or (f) for making a compound of formula I in which $R^3$ is a group of the formula $-NR^4R^5$ in which $R^4$ and $R^5$ are as described above, appropriately amidating a compound of formula I in which $R^3$ is a hydroxy or $C_{1-6}$-alkoxy group, and (g) if desired, converting a compound of formula I obtained in which $R^3$ is a hydroxy group into a pharmaceutically acceptable salt with a base.

Examples of trihalogenated and tetrahalogenated alkanes which can be used in embodiment (a) of the process are chloroform, bromoform, iodoform, carbon tetrachloride and carbon tetrabromide. Chloroform is used in a preferred aspect. The strong base can be, for example, an alkali metal hydroxide such as potassium hydroxide or sodium hydroxide. In a preferred aspect the strong base is used in solid (e.g. powdered) form. The reaction can be carried out in an organic solvent, conveniently in an excess of the ketone of formula III. The reaction is conveniently carried out at an elevated temperature, suitably at the reflux temperature of the reaction mixture.

The leaving atom or group denoted by X or Y in a compound of formula IV or V used as a starting material in embodiment (b) of the process can be, for example, a halogen atom such as a chlorine or bromine atom or an alkanesulphonate or aromatic sulphonate group such as the methanesulphonate or p-toluenesulphonate group.

The reaction in accordance with embodiment (b) of the process can be carried out in the presence of an inert organic solvent such as an aromatic hydrocarbon (e.g. benzene, toluene etc), a halogenated aromatic hydrocarbon (e.g. chlorobenzene etc), dimethylformamide etc. Dimethylformamide is the preferred solvent. The strong base can be, for example, an alkali metal such as sodium or potassium or an alkali metal hydride such as sodium hydride or potassium hydride. The reaction can be carried out at a temperature between about room temperature and the reflux temperature of the reaction mixture, conveniently at about room temperature.

The reaction of a compound of formula VI with a compound of formula VII in accordance with embodiment (c) of the process can be carried out in an inert organic solvent such as aliphatic or cyclic ether (e.g. diethyl ether, tetrahydrofuran, dioxan etc). Suitably, the reaction is carried out at a low temperature, conveniently between about 0° C. and 10° C. and expediently at about 5° C.

The hydrolysis of a compound of formula I in which $R^3$ is a $C_{1-6}$-alkoxy group in accordance with embodiment (d) of the process can be carried out in a manner known per se. For example, the hydrolysis can be carried out by treatment with a suitable base such as an alkali metal hydroxide (e.g. sodium hydroxide or potassium hydroxide) in a solvent such as an alkanol (e.g. methanol or ethanol). Suitably, the hydrolysis is carried out at about room temperature.

The esterification of a compound of formula I in which $R^3$ is a hydroxy group in accordance with embodiment (e) of the process can be carried out in a manner known per se. For example, the esterification can be carried out by treatment with a suitable diazoalkane such as diazomethane. Again, for example, the esterification can be carried out by treatment with an appropriate alcohol (e.g. methanol or ethanol) in the presence of a strong acid such as a hydrohalic acid (e.g. hydrochloric acid) or a sulphonic acid (e.g. p-toluenesulphonic acid). Further, for example, a compound of formula I in which $R^3$ is a hydroxy group can be converted in a known manner into a reactive derivative such as an acid halide (e.g. the acid chloride) or an acid anhydride and this can be reacted with an appropriate alcohol, likewise in a manner known per se.

The amidation of a compound of formula I in which $R^3$ is a hydroxy or $C_{1-6}$-alkoxy group in accordance with embodiment (f) of the process can also be carried out in a manner known per se. For example, the amidation can be carried out by converting a compound of formula I in which $R^3$ is a hydroxy group into a reactive derivative as mentioned earlier and treating this derivative in a known manner with a compound of the formula $HNR^4R^5$ in which $R^4$ and $R^5$ are as described above, i.e. with ammonia, a $C_{1-6}$-alkylamine, a di($C_{1-6}$-alkyl)amine or an appropriate saturated heteromonocyclic amine. Again, for example, a compound of formula I in which $R^3$ is a $C_{1-6}$-alkoxy group can be converted into a corresponding amide by treatment in a known manner with a compound of the formula $HNR^4R^5$ in which $R^4$ and $R^5$ are as described above.

The compounds of formula I in which $R^3$ is a hydroxy group can be converted into pharmaceutically acceptable salts with bases in accordance with embodiment (g) of the process. Examples of such salts are alkali metal salts (e.g. sodium and potassium salts), alkaline earth metal salts (e.g. calcium and magnesium salts), ammonium salts and salts with organic amines (e.g. dicyclohexylamine salts). The salts can be prepared by treating a compound of formula I in which $R^3$ is a hydroxy group with an appropriate base according to known procedures.

A racemic compound of formula I can be resolved into the optical isomers according to methods known per se. For example, a racemic compound of formula I in which $R^3$ is a hydroxy group can be treated with a suitable optically active base such as (+)- or (−)-ephedrine, (+)- or (−)-α-methylbenzylamine or the like, the optically active salts obtained can be separated (e.g. by fractional crystallization) and, where required, the optically uniform compounds can be liberated from these salts by conventional methods. Alternatively, an optically active starting material can be used in the process provided by the invention.

The starting materials used in the process provided by this invention, that is, compounds of formulas II, III, IV, V, VI, and VII, are either known compounds or analogues of known compounds which can be prepared in a similar manner to the known compounds. The Examples hereinafter contain detailed information concerning the preparation of the respective starting materials.

The compounds of formula I and pharmaceutically acceptable salts of the compounds of formula I in which $R^3$ is a hydroxy group with bases possess valuable anti-arthritic activity in warmblooded animals, which can be demonstrated, for example, in the test described hereinafter:

Female rats received an intradermal injection into the shaved backs of 10×0.1 ml of an emulsion of type II collagen/Freund's incomplete adjuvant. Fifteen days later, those rats which had developed bilateral hind paw inflammation were treated with the test compound which was administered orally in a once daily dosage for a further fifteen days. Paw volumes were measured by water-displacement plethysmography and activity was expressed as mean changes in paw volume compared with the pre-treatment volume. Statistical analysis was carried out using the Student's unpaired 't' test. The results obtained using representative compounds of formula I as the test compound are compiled in the following Table.

TABLE

| Compound | Dosage in mg/kg/day | Paw volume Mean change on day 11 compared with day 1 (in ml) |
| --- | --- | --- |
| A | 50 | −0.29 ± 0.05** |
| B | 100 | −0.47 ± 0.06* |
| C | 100 | −0.44 ± 0.11** |
| Control | — | +0.13 ± 0.12 |

*p = 0.05;
**p = 0.01 compared with control (Student's 't' test).
Compound A: 2-[[2-(4-Chlorophenyl)-4-methyl-5-oxazolyl]methoxy]-2-methylpropionic acid.
Compound B: 2-[[2-(4-Chlorophenyl)-4-oxazolyl]methoxy-2-methylpropionic acid.
Compound C: 2-[[2-(4-Chlorophenyl)-5-methyl-4-oxazolyl]methoxy]-2-methylpropionic acid.

The compounds of formula I and the pharmaceutically acceptable salts of compounds of formula I in which $R^3$ is a hydroxy group with bases can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspension. However, the administration can also be carried out rectally, e.g. in the form of suppositories, or parenterally, e.g. in the form of injection solutions.

Medicaments containing a compound of formula I in accordance with the invention and a therapeutically inert carrier are also an object of the present invention. Such medicaments can be manufactured by bringing a compound of formula I in accordance with the invention and, if desired, one or more other therapeutically valuable substances into a galenical administration form together with one or more therapeutically inert excipients.

For the preparation of medicaments the compounds of formula I in accordance with the invention can be processed with pharmaceutically inert, inorganic or organic carriers. Lactose, maize starch or derivatives thereof, talc, stearic acid or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, required in the case of soft gelatine capsules. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils and the like. Suitable carriers for suppositories are, for example, natural or hardened oils, waxes, fats, semi-liquid or liquid polyols and the like.

The medicaments can also contain preserving agents, solubilizing agents, stabilizing agents, wetting agents, emulsifying agents, sweetening agents, colouring agents, flavouring agents, salts for varying the osmotic pressure, buffers, coating agents or antioxidants. They can also contain other therapeutically valuable substances.

As mentioned earlier, the compounds of formula I in accordance with the invention can be used in the control or prevention of illnesses, especially in the control or prevention of arthritis. The dosage can vary within wide limits and is, of course, fitted to a particular person's requirements in each particular case. In the case of oral administration the daily dosage for an adult human lies in a range of about 50 mg to about 2500 mg, and the dosage for a particular individual can be determined by taking into consideration the individual's requirements.

The use of the products in accordance with the invention for the manufacture of medicaments for the control or prevention of arthritis is also an object of the present invention.

The following Examples illustrate the invention:

EXAMPLE 1

6.9 g (30.8 mmol) of 2-(4-chlorophenyl)-4-methyl-5-oxazolemethanol were combined with 6.2 g (155 mmol) of powdered sodium hydroxide in 45 ml of acetone and the suspension was heated to reflux. 4.9 g (41.1 mmol) of chloroform in 10 ml of acetone were added dropwise during 30 minutes and the suspension was heated at reflux for 4 hours. The solvent was removed by evaporation under reduced pressure, and the residue was partitioned between 150 ml of diethyl ether and 400 ml of water. The organic phase was separated and the aqueous phase was extracted twice with diethyl ether. The aqueous phase was acidified to pH 2 with concentrated hydrochloric acid and extracted three times with 50 ml of dichloromethane each time. The combined dichloromethane extracts were dried over magnesium sulphate, filtered and evaporated to yield 3.7 g of crude product. Recrystallization from ethyl acetate yielded 3.1 g (32.5%) of 2-[[2-(4-chlorophenyl)-4-methyl-5-oxazolyl]methoxy]-2-methylpropionic acid of melting point 166°–167° C.

The 2-(4-chlorophenyl)-4-methyl-5-oxazolemethanol used as the starting material was prepared as follows:

(a) A solution of 15.65 g (0.1 mol) of 4-chlorobenzoic acid in 20 ml of dimethylformamide was added dropwise to a stirred suspension of 5.3 g (0.05 mol) of anhydrous sodium carbonate in 80 ml of dimethylformamide. The suspension was heated at 80° C. for 1 hour and a solution of 16.46 g (0.1 mol) of ethyl 2-chloroacetoacetate in 10 ml of dimethylformamide was added. The suspension was heated at 80° C. for 6 hours and left to cool overnight. The solvent was removed by evaporation under reduced pressure and the residue was partitioned between 400 ml of water and 300 ml of diethyl ether. The organic phase was separated and washed twice with 300 ml of water. The organic phase was dried over magnesium sulphate, filtered and the solvent was removed by evaporation under reduced pressure to yield 26.86 g (94%) of ethyl 2-(4-chlorobenzoyloxy)-3-oxo-butyrate in the form of an oil which was homogeneous according to thin-layer chromatography.

(b) 19.6 g (0.2 mol) of concentrated sulphuric acid were added dropwise during 10 minutes to 90 g (2 mol) of formamide, the temperature of the solution being held below 10° C. by external cooling, 26.8 g (0.09 mol) of ethyl 2-(4-chlorobenzoyloxy)-3-oxo-butyrate were added and the stirred solution was heated at 140° C. for 2 hours. The cooled suspension was partitioned between 400 ml of water and 300 ml of diethyl ether. The organic phase was washed twice with 200 ml of 1N hydrochloric acid each time and once with 200 ml of water and then filtered to remove suspended solids. The organic phase was dried over magnesium sulphate, filtered and evaporated. The residue was purified by chromatography on silica gel using 20% by volume ethyl acetate in hexane for the elution. After evaporation of the eluate there were obtained 13.3 g (50%) of ethyl 2-(4-chlorophenyl)-4-methyl-5-oxazolecarboxylate of melting point 80°-81° C.

(c) 9.3 g (35.1 mmol) of ethyl 2-(4-chlorophenyl)-4-methyl-5-oxazolecarboxylate were dissolved in 40 ml of dry tetrahydrofuran and the solution was added dropwise during 10 minutes to a stirred suspension of 1.75 g (46.1 mmol) of lithium aluminium hydride in 60 ml of dry tetrahydrofuran at 0° C. The suspension was stirred at 0° C. for 1 hour and then at room temperature for 1.5 hours. Excess lithium aluminium hydride was destroyed by the dropwise addition of saturated aqueous sodium sulphate, followed by the addition of 100 ml of dilute aqueous sulphuric acid. The aqueous phase was extracted twice with dichloromethane. The combined extracts were washed once with water, dried over magnesium sulphate, filtered and evaporated. The residue was recrystallized from chloroform/hexane to give 6.44 g (82%) of 2-(4-chlorophenyl)-4-methyl-5-oxazolemethanol of melting point 135° C.

EXAMPLE 2

In a manner analogous to that described in Example 1, from 8.5 g (41.1 mmol) of 2-(4-fluorophenyl)-4-methyl-5-oxazolemethanol there were obtained, after recrystallization of the product from ethyl acetate, 3.5 g (29%) of 2-[[2-(4-fluorophenyl)-4-methyl-5-oxazolyl]-methoxy]-2-methylpropionic acid of melting point 166.5°-167.5° C.

The 2-(4-fluorophenyl)-4-methyl-5-oxazolemethanol, melting point 136° C., used as the starting material was prepared in a manner analogous to that described in Example 1(a), (b) and (c).

EXAMPLE 3

In a manner analogous to that described in Example 1, from 13.5 g (57.9 mmol) of 2-(4-trifluoromethylphenyl)-4-methyl-5-oxazolemethanol there were obtained, after recrystallization of the product from ethyl acetate, 5.67 g (28.5%) of 2-[[2-(4-trifluoromethylphenyl)-4-methyl-5-oxazolyl]methoxy]-2-methylpropionic acid of melting point 156°-157° C.

The 2-(4-trifluoromethylphenyl)-4-methyl-5-oxazolemethanol, melting point 141°-142° C., used as the starting material was prepared in a manner analogous to that described in Example 1(a), (b) and (c).

EXAMPLE 4

In a manner analogous to that described in Example 1, from 4.25 g (20.3 mmol) of 2-(4-chlorophenyl)-5-oxazolemethanol there were obtained, after recrystallization of the product from ethyl acetate, 2.2 g (36.6%) of 2-[[2-(4-chlorophenyl)-5-oxazolyl]methoxy]-2-methylpropionic acid of melting point 151.5°-153° C.

The 2-(4-chlorophenyl)-5-oxazolemethanol used as the starting material was prepared as follows:

13.8 ml of a 2.42M (33.4 mmol) solution of n-butyl lithium in hexane were added dropwise during 5 minutes to a stirred solution of 6 g (33.4 mmol) of 2-(4-chlorophenyl)oxazole in 60 ml of dry tetrahydrofuran maintained at −60° C. under an argon atmosphere. The suspension was allowed to warm to −40° C. during 30 minutes and 6.9 g (230 mmol) of paraformaldehyde were added to a slurry in 15 ml of dry tetrahydrofuran. The mixture was allowed to attain room temperature during 1.5 hours and was stirred for a further 1 hour. 10 ml of saturated aqueous ammonium chloride were added to the mixture and the resulting suspension was partitioned between 300 ml of water and 200 ml of dichlormethane. The organic phase was separated and the aqueous phase was extracted twice with 200 ml of dichloromethane each time. The combined organic phases were dried over magnesium sulphate and filtered, and the solvent was removed by evaporation under reduced pressure to given an oil. The oil was chromatographed on silica gel using 70% by volume ethyl acetate in hexane for the elution. The eluate was evaporated to yield 4.25 g (60%) of 2-(4-chlorophenyl)-5-oxazolemethanol of melting point 115°-116° C.

EXAMPLE 5

In a manner analogous to that described in Example 1, but using powdered potassium hydroxide in place of powdered sodium hydroxide, from 7.2 g (34.4 mmol) of 5-(4-chlorophenyl)-2-oxazolemethanol there were obtained, after recrystallization of the product from ethyl acetate, 1.4 g (14%) of 2-[[5-(4-chlorophenyl)-2-oxazolyl]methoxy]-2-methylpropionic acid of melting point 143°-146° C.

The 5-(4-chlorophenyl)-2-oxazolemethanol used as the starting material was prepared as follows:

(a) 12.78 g (50 mmol) of N-[(4-chlorobenzoyl)methyl]-2-ethoxyacetamide were dissolved in 32.5 ml of concentrated sulphuric acid while stirring and cooling intermittently so that the temperature did not rise above room temperature. The mixture was held at room temperature for 20 hours, then poured on to 600 ml of ice/water and extracted three times with 150 ml of diethyl ether each time. The combined ether extracts were washed with 100 ml of saturated sodium hydrogen carbonate solution, then dried over magnesium sulphate, filtered and evaporated to give 10.55 g (89%) of 5-(4-chlorophenyl)-2-ethoxymethyloxazole in the form of a syrup.

(b) 7.5 ml of concentrated sulphuric acid were added carefully to a suspension, cooled in ice, of 1.4 g (5.9 mmol) of 5-(4-chlorophenyl)-2-ethoxymethyl-oxazole in 4.5 ml of water. The resulting solution was stirred and heated at 140° C. under reflux for 4 hours, then cooled and poured on to 140 ml of ice/water. The mixture was extracted three times with 30 ml of dichloromethane each time. The combined dichloromethane extracts were washed with 50 ml of saturated sodium hydrogen carbonate solution, dried over sodium sulphate, filtered and evaporated. Recrystallization of the product from toluene yielded 0.80 g (65%) of 5-(4-chlorophenyl)-2-oxazolemethanol of melting point 100°-103.5° C.

EXAMPLE 6

In a manner analogous to that described in Example 1, from 16 g (76 mmol) of 4-(4-chlorophenyl)-2-oxazolemethanol there were obtained, after recrystallization of the product of toluene, 8.85 g (39%) of 2-[[4-(4-chlorophenyl)-2-oxazolyl]methoxy]-2-methylpropionic acid of melting point 115.5°–118° C.

The 4-(4-chlorphenyl)-2-oxazolemethanol used as the starting material was prepared as follows:

(a) 40 g (0.41 mol) of concentrated sulphuric acid were added dropwise while stirring to 150 g (3.3 mol) of formamide, the temperature of the solution being held below 10° C. by cooling with ice. 50 g (0.2 mol) of (4-chlorobenzoyl)methyl ethoxyacetate were added and the solution was stirred and heated at 140° C. for 2 hours. The mixture was cooled, poured into 2 l of water, acidified to pH 1 by the addition of concentrated hydrochloric acid and extracted once with 500 ml of toluene and then twice with 250 ml of toluene each time. The combined toluene extracts were washed with water, dried over sodium sulphate, filtered and evaporated. The residual syrup was extracted with 700 ml of hot petrol (b.p. 60°–80° C.). The solution was evaporated to dryness and the residue was redissolved in 150 ml of hot petrol (b.p. 40°–60° C.). Upon cooling in acetone/$CO_2$ the product crystallized and was filtered off rapidly and dried to give 21.7 g (47%) of 4-(4-chlorophenyl)-2-ethoxymethyl-oxazole in the form of a soft solid of indeterminate melting point.

(b) 181 ml of a 1M solution of boron trichloride in dichloromethane was added dropwise to a stirred solution of 21.5 g (90.5 mmol) of 4-(4-chlorophenyl)-2-ethoxymethyl-oxazole in 100 ml of dichloromethane. The temperature of the mixture was held below 10° C. during the addition by cooling with ice. After completion of the addition the mixture was stirred at room temperature for 2 hours and then poured on to 500 ml of ice/water. The dichloromethane phase was separated and the aqueous phase was extracted with 100 ml of dichloromethane. The combined dichloromethane extracts were washed with saturated sodium hydrogen carbonate solution, dried over sodium sulphate, filtered and evaporated. Recrystallization of the residue from toluene yielded 15.7 g (83%) of 4-(4-chlorophenyl)-2-oxazolemethanol of melting point 68°–71.5° C.

EXAMPLE 7

In a manner analogous to that described in Example 1, from 23.15 g (90 mmol) of 2-(4-trifluoromethylphenyl)-5-methyl-4-oxazolemethanol there were obtained, after recrystallization of the product from toluene, 8.0 g (26%) of 2-[[2-(4-trifluoromethylphenyl)-5-methyl-4-oxazolyl]methoxy]-2-methylpropionic acid in the form of a cream coloured crystalline solid of melting point 146°–147° C.

The 2-(4-trifluoromethylphenyl)-5-methyl-4-oxazolemethanol used as the starting material was prepared as follows:

(a) 34.8 g (0.20 mol) of 4-trifluoromethylbenzaldehyde and 20.2 g (0.20 mol) of 2,3-butanedione monoxime were dissolved in 100 ml of glacial acetic acid and the mixture was stirred at room temperature while passing gaseous hydrogen chloride through the mixture until a saturated solution was obtained. The mixture was stirred at room temperature overnight and then treated with an excess of anhydrous diethyl ether. The colourless crystalline precipitate was filtered off, washed free of mother liquors using fresh anhydrous diethyl ether and dried in vacuo to give 50 g (86%) of 2-(4-trifluoromethylphenyl)-4,5-dimethyloxazole N-oxide hydrochloride of melting point 175°–177° C. (decomposition).

(b) 50 g of the above N-oxide hydrochloride were added to a suspension of 14 g (0.17 mol) of finely divided anhydrous sodium acetate in 100 ml of acetic anhydride, the mixture was stirred until the resulting exothermic reaction had slowed and was finally heated to about 140° C. for 4 hours. The mixture was cooled, and the inorganic precipitate was filtered off and washed with toluene. The combined organic solutions were concentrated in vacuo and the residue was partitioned between dichloromethane and excess aqueous 2N sodium carbonate solution. The organic phase was separated, washed twice with water, dried over magnesium sulphate, filtered through silica gel and concentrated in vacuo to give 30 g (60%) of 4-acetoxymethyl-2-(4-trifluoromethylphenyl)-5-methyl-oxazole in the form of a pale yellow semi-crystalline solid which was homogeneous according to thin-layer chromatography.

(c) 30 g of the above ester were dissolved in 400 ml of ethanol and the solution was treated with 300 ml of aqueous 2N sodium hydroxide. The mixture was stirred at room temperature overnight, then concentrated in vacuo and the residue was partitioned between dichloromethane and water. The aqueous phase was separated and washed with two further portions of dichloromethane. The combined organic phases were washed twice with water, dried over magnesium sulphate, filtered and concentrated in vacuo to give 23 g (90%) of 2-(4-trifluoromethylphenyl)-5-methyl-4-oxazolemethanol in the form of a yellow-brown solid. Recrystallization from cyclohexane in the presence of decolourizing charcoal gave 2-(4-trifluoromethylphenyl)-5-methyl-4-oxazolemethanol in the form of a cream coloured crystalline solid of melting point 98°–99° C.

EXAMPLE 8

In a manner analogous to that described in Example 1, from 11.2 g (50 mmol) of 2-(4-chlorophenyl)-5-methyl-4-oxazolemethanol there were obtained, after recrystallization of the product from toluene, 2.7 g (17.4%) of 2-[[2-(4-chlorophenyl)-5-methyl-4-oxazolyl]methoxy]-2-methylpropionic acid in the form of a colourless crystalline solid of melting point 123°–124° C.

The 2-(4-chlorophenyl)-5-methyl-4-oxazolemethanol used as the starting material was prepared either by reducing the known 2-(4-chlorophenyl)-5-methyl-4-oxazolecarboxylic acid with lithium aluminium hydride in a manner analogous to that described by Meguro and Fujita, European Patent Publication No. 96,890, or in Example 1(c) hereinbefore, or from 2-(4-chlorophenyl)-4,5-dimethyloxazole N-oxide in a manner analogous to that described in Example 7(b) and (c) hereinbefore. By using either method there was obtained 2-(4-chlorophenyl)-5-methyl-4-oxazolemethanol of melting point 130°–131° C. (from cyclohexane).

EXAMPLE 9

In a manner analogous to that described in Example 1, from 6.5 g (31.4 mmol) of 2-(4-fluorophenyl)-5-methyl-4-oxazolemethanol there were obtained, after recrystallization of the product from toluene, 1.5 g (17%) of 2-[[2-(4-fluorophenyl)-5-methyl-4-oxazolyl]methoxy]-2-methylpropionic acid in the form of a colourless crystalline solid of melting point 118°–120° C.

The 2-(4-fluorophenyl)-5-methyl-4-oxazolemethanol used as the starting material was prepared in a manner analogous to the methods described in Example 8 by reducing the known 2-(4-fluorophenyl)-5-methyl-4-oxazolecarboxylic acid with lithium aluminium hydride or by rearranging 2-(4-fluorophenyl)-4,5-dimethyl-oxazole N-oxide in acetic anhydride followed by aqueous-alcoholic alkaline hydrolysis. By using either method there was obtained 2-(4-fluorophenyl)-5-methyl-4-oxazolemethanol of melting point 153°–155° C. (from cyclohexane).

EXAMPLE 10

A solution of 1.55 g (13.2 mmol) of methyl 2-hydroxy-2-methylpropionate in 4 ml of dimethylformamide was added during 1 hour to a stirred suspension of 0.53 g (13.2 mmol) of a 60% sodium hydride dispersion in mineral oil in 8 ml of dry dimethylformamide. The solution was stirred at room temperature for 1 hour and was then added slowly to a solution of 2 g (9.4 mmol) of 2-(4-chlorophenyl)-4-chloromethyl-oxazole in 4 ml of dry dimethylformamide at 0° C. under an argon atmosphere. The mixture was stirred at room temperature overnight and 2 ml of saturated aqueous ammonium chloride were then added. The majority of the solvent was removed by evaporation under reduced pressure and the residue was partitioned between 100 ml of diethyl ether and 100 ml of water. The organic phase was separated, washed with 100 ml of water and dried over magnesium sulphate. The organic solution was filtered and evaporated to give 2.7 g of a crude solid. This solid was dissolved in 100 ml of ethanol and 0.4 g (10 mmol) of sodium hydroxide in 5 ml of water was added. The solution was heated at reflux for 1 hour, cooled and the majority of the solvent was removed under reduced pressure. The solid residue was dissolved in 400 ml of water and extracted twice with 100 ml of diethyl ether each time. The aqueous phase was acidified to pH 2 with concentrated hydrochloric acid and extracted three times with 100 ml of dichloromethane each time. The combined dichloromethane extracts were dried over magnesium sulphate, filtered and evaporated to give a solid which was recrystallized from ethyl acetate. There were obtained 1.6 g (57%) of 2-[[2-(4-chlorophenyl)-4-oxazolyl]methoxy]-2-methylpropionic acid of melting point 144.5°–145° C.

The 2-(4-chlorophenyl)-4-chloromethyl-oxazole used as the starting material was prepared as described in British Patent Specification No. 1,139,940.

EXAMPLE 11

3.57 g (37 mmol) of triethylamine in 30 ml of dry dimethylformamide were added during 10 minutes while stirring and cooling at 10° C. to a solution of 6.33 g (33.3 mmol) of 4-chlorobenzene N-hydroxycarboximidoyl chloride in 60 ml of dry dimethylformamide. After 1 hour at 20° C. the solution of 4-chlorobenzonitrile oxide formed was poured into water and filtered off. The moist solid was dissolved in 150 ml of diethyl ether and dried twice with 10 g of molecular sieve (3A) each time. The ethereal solution was filtered and there were added thereto at 5° C. 6.56 g (36.6 mmol) of methyl 2-propynyloxy-2-methylpropionate in 25 ml of diethyl ether. After 24 hours the ether was removed and the product was purified by column chromatography on 220 g of silica gel using hexane/ethyl acetate (4:1) and then hexane/ethyl acetate (2:1) for the elution. There were obtained 4.67 g of methyl 2-[[3-(4-chlorophenyl)-5-isoxazolyl]methoxy]-2-methylpropionate in the form of a colourless oil having a purity of 99% according to high pressure liquid chromatography.

The methyl 2-propynyloxy-2-methylpropionate used as the starting material was prepared as follows:

55 g (0.47 mol) of methyl 2-hydroxy-2-methylpropionate in 400 ml of dry dimethylformamide were added dropwise while stirring during 0.75 hour to 14 g (0.47 mol, 80% oil dispersion) of sodium hydride in 200 ml of dry dimethylformamide. After 3 hours at 20° C. 62.5 g (0.42 mol) of propargyl bromide (as a 80% solution in toluene) in 200 ml of dimethylformamide was added during 0.5 hour while cooling to maintain the temperature below 25° C. After stirring at 20° C. for 17 hours the mixture was poured on to ice and extracted with toluene. The toluene phase was evaporated carefully and the residue was distilled at 80° C./15 mmHg to give 26.8 g (41%) of methyl 2-propynyloxy-2-methylpropionate.

EXAMPLE 12

1.3 ml of 1N sodium hydroxide solution were added to 0.31 g (1.0 mmol) of methyl 2-[[3-(4-chlorophenyl)-5-isoxazolyl]methoxy-2-methylpropionate in 10 ml of methanol. After 64 hours at 20° C. the methanol was removed by evaporation and the product was isolated by acidification with 2N hydrochloric acid and extraction with diethyl ether. Crystallization from toluene/hexane gave 0.17 g (58%) of 2-[[3-(4-chlorophenyl)-5-isoxazolyl]methoxy]-2-methylpropionic acid of melting point 130°–134° C.

EXAMPLE 13

In a manner analogous to that described in Example 1, but using powdered potassium hydroxide in place of sodium hydroxide, from 5 g (24 mmmol) of 5-(4-chlorophenyl)-3-isoxazolemethanol there were obtained, after recrystallization of the product from toluene/hexane, 1.06 g (15%) of 2-[[5-(4-chlorophenyl)-3-isoxazolyl]methoxy]-2-methylpropionic acid of melting point 115°–118° C.

The 5-(4-chlorophenyl)-3-isoxazolemethanol used as the starting material was prepared as follows:

(a) Ethyl 5-(4-chlorophenyl)-3-isoxazolecarboxylate, melting point 124°–126° C., was prepared according to the general isoxazole synthesis described by P. G. Baraldi et al., J. Het. Chem., 1982, 19, 557.

(b) 4.75 g (19 mmol) of the above ester were dissolved in 30 ml of diethyl ether under a nitrogen atmosphere and a slurry of 1.05 g (48 mmol) of lithium borohydride in 5 ml of diethyl ether was added dropwise thereto. The mixture was stirred at 20° C. for 15 minutes, warmed gradually to reflux and maintained at reflux for 3.5 hours. The mixture was then poured on to ice/water, extracted with diethyl ether, and the combined ether extracts were dried over magnesium sulphate, filtered and evaporated. Recrystallization of the residue from toluene yielded 2.8 g (71%) of 5-(4-chlorophenyl)-3-isoxazolemethanol of melting point 93°–95° C.

EXAMPLE 14

In a manner analogous to that described in Example 1, but using powdered potassium hydroxide in place of sodium hydroxide, from 5 g (22.4 mmol) of 3-(4-chlorophenyl)-5-isoxazolyl-2-ethanol there was obtained, after recrystallization of the product from ethyl acetate/hexane, 0.9 g (13%) of 2-[2-[3-(4-chlorophenyl)-5-isoxazolyl]ethoxy]-2-methylpropionic acid of melting point 98°–100° C.

The 3-(4-chlorophenyl)-5-isoxazolyl-2-ethanol used as the starting material was prepared as follows:

5.05 g (5 mmol) of triethylamine in 20 ml of diethyl ether were added dropwise at −10° C. to a solution of 3.86 g (5.5 mmol) of 3-butyn-1-ol and 9.50 g (5 mmol) of 4-chlorobenzene N-hydroxycarboximidoyl chloride in 200 ml of dry diethyl ether. After 3 hours the reaction mixture was filtered, the filtrate was evaporated and the residue was recrystallized from ethyl acetate/hexane to yield 6.15 g (55%) of 3-(4-chlorophenyl)-5-isoxazolyl-2-ethanol of melting point 65.5°–67.5° C. after crystallization from ethyl acetate.

EXAMPLE 15

2.02 g (0.02 mol) of triethylamine in 20 ml of diethyl ether were added dropwise over a period of 15 minutes at −10° C. to a solution of 4.49 g (0.02 mol) of 3,4-dichlorobenzene N-hydroxycarboximidoyl chloride in 90 ml of dry diethyl ether. After 0.5 hour at −5° C. to −10° C. 4.004 g (0.022 mol) of methyl 2-propynyloxy-2-methylpropionate were added and the mixture was stored at −5° C. for 48 hours. The mixture was filtered, the filtrate was evaporated and the residue was chromatographed on 150 g of silica gel using hexane/ethyl acetate (4:1) for the elution. There were obtained 6 g (87%) of pure methyl 2-[[3-(3,4-dichlorophenyl)-5-isoxazolyl]methoxy]-2-methylpropionate in the form of an oil.

Microanalysis for $C_{15}H_{15}Cl_2NO_4$: Calculated: C: 52.34; H: 4.39; N: 4.07%. Found: C: 52.57; H: 4.38; N: 4.15%.

EXAMPLE 16

In a manner analogous to that described in Example 12, from 1.88 g (5 mmol) of methyl 2-[[2-(3,4-dichlorophenyl)-5-isoxazolyl]methoxy]-2-methylpropionate there were obtained, after recrystallization of the product from ethyl acetate, 1.11 g (69%) of 2-[[3-(3,4-dichlorophenyl)-5-isoxazolyl]methoxy]-2-methylpropionic acid of melting point 129°–131° C.

EXAMPLE 17

In a manner analogous to that described in Example 1, but using powdered potassium hydroxide in place of sodium hydroxide, from 5 g (22.4 mmol) of 3-(4-chlorophenyl)-5-isoxazolyl-1-ethanol there was obtained, after recrystallization of the product from ethyl acetate/hexane, 0.7 g (10%) of 2-[1(RS)-[3-(4-chlorophenyl)-5-isoxazolyl]ethoxy]-2-methylpropionic acid of melting point 141°–143° C.

The resolution of the above (RS)-acid was carried out as follows:

A mixture of 6.18 g (200 mmol) of the (RS)-acid and 3.32 g (200 mmol) of (+)-ephedrine was recrystallized from 20 ml of isopropanol. The crystals were recrystallized six times from isopropanol to give pure (−)-acid ephedrine salt. The salt was partitioned between 2N hydrochloric acid and diethyl ether. The ether extract was dried over sodium sulphate, filtered and evaporated to yield, after recrystallization from ethyl acetate/hexane, (−)-2-[1-[3-(4-chlorophenyl)-5-isoxazolyl]ethoxy]-2-methylpropionic acid of melting point 121°–125° C.; $[\alpha]_{589} = -96.1°$ (c=1% in ethanol).

In a manner analogous to that described in the preceding paragraph, but using (−)-ephedrine in place of (+)-ephedrine, there was obtained (+)-2-[1-[3-(4-chlorophenyl)-5-isoxazolyl]ethoxy]-2-methylpropionic acid of melting point 120°–124° C.; $[\alpha]_{589} = +94.7°$ (c=1% in ethanol).

The 3-(4-chlorophenyl)-5-isoxazolyl-1-ethanol used as the starting material was prepared as follows:

In a manner analogous to that described in the second paragraph of Example 14, using 1.93 g (27 mmol) of 3-butyn-2-ol there were obtained, after recrystallization from methylcyclohexane, 3.82 g (68%) of 3-(4-chlorophenyl)-5-isoxazolyl-1-ethanol of melting point 63°–65° C.

EXAMPLE 18

A mixture of 4.9 g (25 mmol) of 5-chlorothiophene N-hydroxycarboximidoyl chloride and 4.54 g (27 mmol) of methyl 2-propynyloxy-2-methylpropionate in 180 ml of dry diethyl ether was treated with a solution of 2.53 g (25 mmol) of triethylamine in 20 ml of dry diethyl ether while stirring under nitrogen. After 3 days at 20° C. the mixture was filtered and the filtrate was evaporated to give 6.6 g of crude methyl 2-[[3-(5-chlorothien-2-yl)-5-isoxazolyl]methoxy]-2-methylpropionate in the form of an oil. 6.3 g of this oil, without further purification, were hydrolyzed in a manner analogous to that described in Example 12 to yield, after crystallization from ethyl acetate/hexane 2.1 g (28%) of 2-[[3-(5-chlorothien-2-yl)-5-isoxazolyl]methoxy]-2-methylpropionic acid of melting point 128°–130° C.

EXAMPLE 19

1.3 g of oxalyl chloride were added dropwise to 3 g (100 mmol) of 2-[[3-(4-chlorophenyl)-5-isoxazolyl]methoxy]-2-methylpropionic acid in 100 ml of diethyl ether. After 4 hours at 20° C. the diethyl ether was removed under reduced pressure and the acid chloride was taken up in 75 ml of tetrahydrofuran and added to a solution of tetrahydrofuran saturated with ammonia gas. After 1.5 hours the heavy white precipitate was removed by filtration, the filtrate was evaporated and the resulting 2.46 g (82%) of 2-[[3-(4-chlorophenyl)-5-isoxazolyl]methoxy]-2-methylpropionamide was crystallized from ethanol; melting point 154°–155° C.

EXAMPLE 20

In a manner analogous to that described in Example 19, but using methylamine in dry diethyl ether in place of the solution of tetrahydrofuran saturated with ammonia gas, there was obtained 2-[[3-(4-chlorophenyl)-5-isoxazolyl]methoxy]-N,2-dimethylpropionamide of melting point 93°–94° C. after crystallization from ethyl acetate.

EXAMPLE 21

In a manner analogous to that described in Example 19, but using piperidine in dry diethyl ether in place of the solution of tetrahydrofuran saturated with ammonia gas, there was obtained 3-(4-chlorophenyl)-5-[[1-methyl-1-(piperidinocarbonyl)ethoxy]methyl]isoxazole of melting point 239°–242° C. after crystallization from ethyl acetate/hexane.

EXAMPLE 22

In a manner analogous to that described in Example 1, from 5.17 g (20 mmol) of 2-(3,4-dichlorophenyl)-4-methyl-5-oxazolemethanol there were obtained, after recrystallization of the product from ethyl acetate/hexane, 1.69 g (24.6%) of 2-[[2-(3,4-dichlorophenyl)-4- methyl-5-oxazolyl]methoxy]-2-methylpropionic acid of melting point 130°–131° C.

The 2-(3,4-dichlorophenyl)-4-methyl-5-oxazolemethanol, melting point 158°–159° C., used as the starting material was prepared in a manner analogous to that described in Example 1(a), (b) and (c).

EXAMPLE 23

In a manner analogous to that described in Example 1, from 4.6 g (20.6 mmol) of 2-(3-chlorophenyl)-4-methyl-5-oxazolemethanol there were obtained, after recrystallization of the crude product from ethyl acetate/hexane, 1.2 (18.8%) of 2-[[2-(3-chlorophenyl)-4-methyl-5-oxazolyl]methoxy]-2-methylpropionic acid of melting point 117° C.

The 2-(3-chlorophenyl)-4-methyl-5-oxazolemethanol, melting point 123° C., used as the starting material was prepared in a manner analogous to that described in Example 1(a), (b) and (c).

EXAMPLE 24

In a manner analogous to that described in Example 1, from 5 g (21.3 mmol) of 4-methyl-2-[4-(methylthio)phenyl]-5-oxazolemethanol there was obtained, after recrystallization of the crude product from ethyl acetate/hexane, 0.4 g (6%) of 2-methyl-2-[[4-methyl-2-[4-(methylthio)phenyl]-5-oxazolyl]methoxy]propionic acid of melting point 128° C.

The 4-methyl-2-[4-(methylthio)phenyl]-5-oxazolemethanol, melting point 130° C., used as the starting material was prepared in a manner analogous to that described in Example 1(a), (b) and (c).

EXAMPLE 25

4.44 g (14.5 mmol) of 2-[[2-(4-chlorophenyl)-4-methyl-5-oxazolyl]methoxy]-2-methylpropionic acid were dissolved in 40 ml of dry dichloromethane and 1 drop of dimethylformamide was added. 1.96 (16 mmol) of thionyl chloride were added and the mixture was heated to reflux for 4 hours. The cooled solution of the resulting acid chloride was added while stirring to 70 ml of aqueous ammonium hydroxide solution (specific gravity 1.880) and crushed ice. After stirring for 16 hours the suspension was extracted with 200 ml of dichloromethane. The organic phase was separated and washed twice with 100 ml of water each time. The organic phase was dried over magnesium sulphate and filtered, and the solvent was then removed by evaporation under reduced pressure. Recrystallization of the crude solid from ethyl acetate gave 2.2 g (49%) of 2-[[2-(4-chlorophenyl)-4-methyl-5-oxazolyl]methoxy]-2-methylpropionamide of melting point 177°–178° C.

EXAMPLE 26

4.44 g (14.5 mmol) of 2-[[2-(4-chlorophenyl)-4-methyl-5-oxazolyl]methoxy]-2-methylpropionic acid were dissolved in 40 ml of dry dichloromethane and 1 drop of dimethylformamide was added. 1.9 g (16 mmol) of thionyl chloride were added and the mixture was heated to reflux for 4 hours. 70 ml of ethanol were added slowly to a stirred solution of the thus-obtained acid chloride at 0° C. and the mixture was stirred for 18 hours. The solvent was removed under reduced pressure and the residue was purified by chromatography on silica gel using 17% by volume ethyl acetate in hexane for the elution. After evaporation of the eluate there were obtained 2.8 g (57.2%) of ethyl 2-[[2-(4-chlorophenyl)-4-methyl-5-oxazolyl]methoxy]-2-methylpropionate of melting point 75°–76° C.

EXAMPLE 27

In a manner analogous to that described in Example 1, from 2 g (8.4 mmol) of 2-(4-chlorophenyl)-4-ethyl-5-oxazolemethanol there were obtained, after recrystallization from ethyl acetate/hexane, 1.09 g (40%) of 2-[[2-(4-chlorophenyl)-4-ethyl-5-oxazolyl]methoxy]-2-methylpropionic acid of melting point 133.5°–134.5° C.

The 2-(4-chlorophenyl)-4-ethyl-5-oxazolemethanol, melting point 135°–136° C., used as the starting material was prepared in a manner analogous to that described in Example 1(a), (b) and (c) from 4-chlorobenzoic acid and ethyl 2-chloro-3-oxopentanoate.

EXAMPLE 28

A solution of 0.8 g (5.5 mmol) of methyl 2-hydroxy-2-ethylbutyrate in 2 ml of dimethoxyethane was added over a period of about 10 minutes to a stirred suspension of 0.24 g (6 mmol) of a 60% sodium hydride dispersion in mineral oil in 4 ml of dry dimethoxyethane. The solution was stirred at room temperature for 10 minutes and then a solution of 1.21 g (5 mmol) of 2-(4-chlorophenyl)-4-methyl-5-chloromethyloxazole in 5 ml of dry dimethoxyethane was added. A small crystal of sodium iodide was added and the mixture was stirred at room temperature overnight under an argon atmosphere. The mixture was heated at 65° C. for 1 hour, cooled and 2 ml of water were added. The majority of the solvent was removed by evaporation under reduced pressure and the residue was partitioned between 100 ml of diethyl ether and 100 ml of water. The organic phase was separated, washed with 50 ml of water and dried over magnesium sulphate. After filtration the filtrate was evaporated and the residue was combined with 25 ml of ethanol, 0.3 g (7.5 mmol) of sodium hydroxide and 10 ml of water. The solution was heated at reflux for 40 minutes, cooled and the majority of the solvent was removed under reduced pressure. The residue was dissolved in 100 ml of water and extracted twice with 100 ml of diethyl ether. The aqueous was acidified to pH 2 with concentration hydrochloric acid and extracted three times with 35 ml of dichloromethane each time. The combined dichloromethane extracts were dried over magnesium sulphate, filtered and evaporated to give a crude solid which was recrystallized twice from ethyl acetate/hexane. There was obtained 0.6 g (33%) of 2-[[2-(4-chlorophenyl)-4-methyl-5-oxazolyl]methoxy]-2-ethylbutyric acid of melting point 157° C.

EXAMPLE 29

In a manner analogous to that described in Example 1, from 5.5 g (23 mmol) of 2-(4-chlorophenyl)-4-methyl-5-(2-hydroxyethyl)oxazole there was obtained, after recrystallization of the crude product from ethyl acetate/hexane, 0.4 g (5.2%) of 2-[2-[2-(4-chlorophenyl)-4-methyl-5-oxazolyl]ethoxy]-2-methylpropionic acid of melting point 114°–115° C.

The 2-(4-chlorophenyl)-4-methyl-5-(2-hydroxyethyl)oxazole used as the starting material was prepared according to the method described in Acta Pharmaceutica Suecica, 1967, 4(S), 269–280.

EXAMPLE 30

In a manner analogous to that described in Example 1, but using ethyl methyl ketone in place of acetone, from 3.5 g (15.6 mmol) of 2-(4-chlorophenyl)-4-methyl- 5-oxazolemethanol there was obtained, after recrystallization of the crude product from toluene, 0.47 g (9.27%) of 2-[[2-(4-chlorophenyl)-4-methyl-5-oxazolyl]methoxy]-2-methylbutyric acid of melting point 143°–144° C.

EXAMPLE 31

In a manner analogous to that described in Example 10, from 5.2 g (21.5 mmol) of 2-(4-chlorophenyl)-5-chloromethyl-4-methyloxazole there were obtained 7 g of a mixture of methyl 2-[[2-(4-chlorophenyl)-4-methyl-5-oxazolyl]methoxy]-2-methylpropionate and 2-(4-chlorophenyl)-5-methoxymethyl-4-methyloxazole in the approximate ratio of 5:1 as determined by proton NMR spectroscopy. Hydrolysis of this mixture with an excess of aqueous ethanolic sodium hydroxide solution, as described in Example 10, gave 4.0 g (60%) of 2-[[2-(4-chlorophenyl)-4-methyl-5-oxazolyl]methoxy]-2-methylpropionic acid of melting point 166°–167° C., which was identical with the product obtained in Example 1.

Alternatively, the mixture obtained in the preceding paragraph was chromatographed on silica gel using 30% by volume ethyl acetate in hexane for the elution. Evaporation of the eluate from the homogeneous fractions, followed by recrystallization of the residue from hexane gave 5.0 g (72%) of methyl 2-[[2-(4-chlorophenyl)-4-methyl-5-oxazolyl]methoxy]-2-methylpropionate of melting point 88°–90° C.

The 2-(4-chlorophenyl)-5-chloromethyl-4-methyloxazole used as the starting material was prepared from 2-(4-chlorophenyl)-4-methyl-5-oxazolemethanol in a manner analogous to that described in British Patent Specification No. 1,139,940.

EXAMPLE 32

Ethyl 2-hydroxy-2-methylpropionate was reacted with 2-(4-chlorophenyl)-5-chloromethyl-4-methyloxazole in a manner analogous to that described in Example 10 and then the product was chromatographed in a manner analogous to that described in the second paragraph of Example 31. There was obtained, after recrystallization from hexane, ethyl 2-[[2-(4-chlorophenyl)-4-methyl-5-oxazolyl]methoxy]-2-methylpropionate of melting point 71°–73° C. which was identical with the product obtained in Example 26.

EXAMPLE 33

10.0 ml of 1M sodium isopropoxide solution in isopropanol were added to a warm stirred solution of 3.09 g (10 mmol) of 2-[[2-(4-chlorophenyl)-4-methyl-5-oxazolyl]methoxy]-2-methylpropionic acid in 30 ml of isopropanol and the mixture was allowed to cool slowly to give 3.0 g (90%) of sodium 2-[[2-(4-chlorophenyl)-4-methyl-5-oxazolyl]methoxy]-2-methylpropionate in the form of a colourless crystalline solid of melting point 277°–278° C.

The following Examples illustrate dosage forms containing pharmaceutical compositions of the invention.

EXAMPLE A

Tablets containing the following ingredients may be produced in a conventional manner:

| Ingredient | Per tablet |
|---|---|
| Compound A | 50 mg |
| Lactose | 120 mg |
| Maize starch | 75 mg |
| Talc | 4 mg |
| Magnesium stearate | 1 mg |
| Tablet weight | 250 mg |

Compound A is 2-[[2-(4-chlorophenyl)-4-methyl-5-oxazolyl]methoxy]-2-methylpropionic acid.

EXAMPLE B

Capsules containing the following ingredients can be produced in a conventional manner:

| Ingredient | Per capsule |
|---|---|
| Compound A | 100 mg |
| Lactose | 150 mg |
| Maize starch | 20 mg |
| Talc | 5 mg |
| Capsule fill weight | 275 mg |

Compound A is as in Example A.

We claim:

1. A compound of the formula

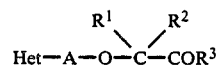

$$\text{Het}-\text{A}-\text{O}-\underset{\underset{R^2}{|}}{\overset{\overset{R^1}{|}}{\text{C}}}-\text{COR}^3 \qquad \text{I}$$

wherein A is $C_{1-6}$-alkylene, Het is a 2-R-oxazol-5-yl, 5-R-oxazol-2-yl, 4-R-oxazol-2-yl, 2-R-oxazol-4-yl, 3-R-isoxazol-5-yl or 5-R-isoxazol-3-yl group which is optionally substituted on the heterocyclic ring by a $C_{1-6}$-alkyl group, R is phenyl or thienyl monosubstituted or disubstituted by halogen, trifluoromethyl or $C_{1-6}$-alkylthio, $R^1$ and $R^2$ each is a $C_{1-6}$-alkyl group and $R^3$ is a hydroxy or $C_{1-6}$-alkoxy group or a group of the formula $-NR^4R^5$ in which $R^4$ and $R^5$ each is a hydrogen atom or a $C_{1-6}$-alkyl group or $R^4$ and $R^5$ together with the nitrogen atom to which they are attached is a 5-membered or 6-membered saturated heteromonocyclic ring which may have an oxygen or sulphur atom or an additional nitrogen atom, or a pharmaceutically acceptable salt of a compound of formula I in which $R^3$ is a hydroxy group with a base.

2. A compound in accordance with claim 1, wherein A is methylene, R is phenyl monosubstituted or disubstituted by halogen or trifluoromethyl and $R^3$ is a hydroxy or $C_{1-6}$-alkoxy group or a group of the formula $-NR^4R^5$ in which $R^4$ and $R^5$ each is a hydrogen atom or a $C_{1-6}$-alkyl group.

3. A compound in accordance with claim 1, wherein A is methylene, 1,1-ethylene or 1,2-ethylene.

4. A compound in accordance with claim 1, wherein Het is a 2-R-oxazol-5-yl group which is optionally substituted by a $C_{1-6}$-alkyl group.

5. A compound in accordance with of claim 1, wherein R is monohalophenyl.

6. A compound in accordance with claim 1, wherein $R^1$ and $R^2$ each is methyl.

7. A compound in accordance with claim 1, wherein $R^3$ is a hydroxy group.

8. A compound in accordance with claim 1, 2-[[2-(4-Chlorophenyl)-4-methyl-5-oxazolyl]methoxy]-2-methylpropionic acid, or the sodium salt thereof.

9. A compound in accordance with claim 1, selected from the group consisting of

2-[[2-(3,4-dichlorophenyl)-4-methyl-5-oxazolyl]methoxy]-2-methylpropionic acid,

2-[[2-(3-chlorophenyl)-4-methyl-5-oxazolyl]methoxy-2-methylpropionic acid, 2-methyl-2-[[4-methyl-2-[4-(methylthio)phenyl]-5-oxazolyl]methoxy]propionic acid, 2-[[2-(4-chlorophenyl)-4-methyl-5-oxazolyl]methoxy]-2-methylpropionamide, ethyl 2-[[2-(4-chlorophenyl)-4-methyl-5-oxazolyl]methoxy]-2-methylpropionate, 2-[[2-(4-chlorophenyl)-4-ethyl-5-oxazolyl]methoxy]-2-methylpropionic acid, 2-[[2-(4-chlorophenyl)-4-methyl-5-oxazolyl]methoxy]-2-ethylbutyric acid, 2-[2-[2-(4-chlorophenyl)-4-methyl-5-oxazolyl]ethoxy]-2-methylpropionic acid, 2-[[2-(4-chlorophenyl)-4-methyl-5-oxazolyl]methoxy]-2-methylbutyric acid, methyl 2-[[2-(4-chlorophenyl)-4-methyl-5-oxazolyl]methoxy]-2-methylpropionate, 2-[2-[3-(4-chlorophenyl)-5-isoxazolyl]ethoxy]-2-methylpropionic acid, methyl 2-[[3-(3,4-dichlorophenyl)-5-isoxazolyl]methoxy]-2-methylpropionate, 2-[[3-(3,4-dichlorophenyl)-5-isoxazolyl]methoxy]-2-methylpropionic acid, 2-[1-[3-(4-chlorophenyl)-5-isoxazolyl]ethoxy]-2-methylpropionic acid, 2-[[3-(5-chlorothien-2-yl)-5-isoxazolyl]methoxy]-2-methylpropionic acid, 2-[[3-(4-chlorophenyl)-5-isoxazolyl]methoxy]-2-methylpropionamide, 2-[[3-(4-chlorophenyl)-5-isoxazolyl]methoxy]-N,2-dimethylpropionamide and 3-(4-chlorophenyl)-5-[[1-methyl-1-(piperidinocarbonyl)ethoxy]methyl]isoxazole.

10. A compound in accordance with claim 2, selected from the group consisting of 2-[[2-(4-Fluorophenyl)-4-methyl-5-oxazolyl]methoxy]-2-methylpropionic acid, 2-[[2-(4-trifluoromethylphenyl)-4-methyl-5-oxazolyl]methoxy]-2-methylpropionic acid, 2-[[2-(4-chlorophenyl)-5-oxazolyl]methoxy]-2-methylpropionic acid, 2-[[5-(4-chlorophenyl)-2-oxazolyl]methoxy]-2-methylpropionic acid, 2-[[4-(4-chlorophenyl)-2-oxazolyl]methoxy]-2-methylpropionic acid, 2-[[2-(4-trifluoromethylphenyl)-5-methyl-4-oxazolyl]methoxy]-2-methylpropionic acid, 2-[[2-(4-chlorophenyl)-5-methyl-4-oxazolyl]methoxy]-2-methylpropionic acid, 2-[[2-(4-fluorophenyl)-5-methyl-4-oxazolyl]methoxy]-2-methylpropionic acid, 2-[[2-(4-chlorophenyl)-4-oxazolyl]methoxy]-2-methylpropionic acid, 2-[[3-(4-Chlorophenyl)-5-isoxazolyl]methoxy]-2-methylpropionic acid, 2-[[5-(4-chlorophenyl)-3-isoxazolyl]methoxy]-2-methylpropionic acid and methyl 2-[[3-(4-chlorophenyl)-5-isoxazolyl]methoxy]-2-methylpropionate.

11. A composition for treating arthritis comprising a compound of the formula

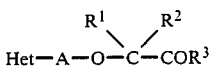

wherein A is $C_{1-6}$-alkylene, Het is a 2-R-oxazol-5-yl, 5-R-oxazol-2-yl, 4-R-oxazol-2-yl, 2-R-oxazol-4-yl, 3-R-isoxazol-5-yl or 5-R-isoxazol-3-yl group which is optionally substituted on the heterocyclic ring by a $C_{1-6}$-alkyl group, R is phenyl or thienyl monosubstituted or disubstituted by halogen, trifluoromethyl or $C_{1-6}$-alkylthio, $R^1$ and $R^2$ each is a $C_{1-6}$-alkyl group and $R^3$ is a hydroxy or $C_{1-6}$-alkoxy group or a group of the formula $-NR^4R^5$ in which $R^4$ and $R^5$ each is a hydrogen atom or a $C_{1-6}$-alkyl group or $R^4$ and $R^5$ together with the nitrogen atom to which they are attached is a 5-membered or 6-membered saturated heteromonocyclic ring which may have an oxygen or sulphur atom or an additional nitrogen atom, or a pharmaceutically acceptable salt of a compound of formula I in which $R^3$ is a hydroxy group with a base, and a pharmaceutically inert, inorganic or organic carrier.

12. A composition in accordance with claim 11, wherein A is methylene, 1,1-ethylene or 1,2-ethylene.

13. A composition in accordance with claim 11 wherein Het is a 2-R-oxazol-5-yl group which is substituted by a $C_{1-6}$-alkyl group.

14. A composition in accordance with claim 11, wherein the compound of formula I is 2-[[2-(4-chlorophenyl)-4-methyl-5-oxazolyl]methyloxy]-2-methylpropionic acid, or the sodium salt thereof.

15. A method for treating arthritis which comprises administering an anti-arthritically effective amount of a compound of the formula

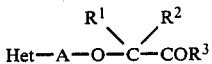

wherein A is $C_{1-6}$-alkylene, Het is a 2-R-oxazol-5-yl, 5-R-oxazol-2-yl, 4-R-oxazol-2-yl, 2-R-oxazol-4-yl, 3-R-isoxazol-5-yl or 5-R-isoxazol-3-yl group which is optionally substituted on the heterocyclic ring by a $C_{1-6}$-alkyl group, R is phenyl or thienyl monosubstituted or disubstituted by halogen, trifluoromethyl or $C_{1-6}$-alkylthio, $R^1$ and $R^2$ each is a $C_{1-6}$-alkyl group and $R^3$ is a hydroxy or $C_{1-6}$-alkoxy group or a group of the formula $-NR^4R^5$ in which $R^4$ and $R^5$ each is a hydrogen atom or a $C_{1-6}$-alkyl group or $R^4$ and $R^5$ together with the nitrogen atom to which they are attached is a 5-membered or 6-membered saturated heteromonocyclic ring which may have an oxygen or sulphur atom or an additional nitrogen atom, or a pharmaceutically acceptable salt of a compound of formula I in which $R^3$ is a hydroxy group with a base.

16. A method in accordance with claim 15, wherein A is methylene, 1,1-ethylene, or 1,2-ethylene.

17. A method in accordance with claim 15, wherein Het is a 2-R-oxazol-5-yl group which is substituted by a $C_{1-6}$-alkyl group.

18. A method in accordance with claim 15, wherein the compound of formula I is 2-[[2-(4-chlorophenyl)-4-methyl-5-oxazolyl]methoxy]-2-methylpropionic acid, or the sodium salt thereof.

* * * * *